(12) United States Patent
Porter et al.

(10) Patent No.: US 8,337,692 B2
(45) Date of Patent: Dec. 25, 2012

(54) ELECTROCHEMICAL DETECTION OF A METAL—LABELLED ANALYTE

(75) Inventors: Robert Andrew Porter, Wymington (GB); Mateusz Szymanski, Teddington (GB)

(73) Assignee: The Secretary of State for Innovation, Universities and Skills of Her Majesty's Britannic Government, London (GB)

( * ) Notice: Subject to any disclaimer, the term of this patent is extended or adjusted under 35 U.S.C. 154(b) by 150 days.

(21) Appl. No.: 12/744,645

(22) PCT Filed: Nov. 25, 2008

(86) PCT No.: PCT/GB2008/003931
§ 371 (c)(1),
(2), (4) Date: Aug. 6, 2010

(87) PCT Pub. No.: WO2009/068862
PCT Pub. Date: Jun. 4, 2009

(65) Prior Publication Data
US 2010/0320092 A1    Dec. 23, 2010

(30) Foreign Application Priority Data

Nov. 26, 2007 (GB) .................................. 0723137.6
Jul. 10, 2008 (GB) .................................. 0812679.9
Jul. 14, 2008 (GB) .................................. 0812845.6

(51) Int. Cl.
*G01N 27/26* (2006.01)
(52) U.S. Cl. .................... 205/792; 435/960; 204/403.01
(58) Field of Classification Search ........ 204/403.01–403.15; 205/792; 435/960
See application file for complete search history.

(56) References Cited

U.S. PATENT DOCUMENTS

| 5,863,502 | A  | 1/1999  | Southgate et al. |
| 6,300,141 | B1 | 10/2001 | Segal et al. |
| 6,319,469 | B1 | 11/2001 | Mian et al. |
| 7,045,364 | B2 | 5/2006  | Limoges et al. |

(Continued)

FOREIGN PATENT DOCUMENTS

EP    1611836    1/2006

(Continued)

OTHER PUBLICATIONS

Wang, Chuan-yi, Liu, Chun-yan, Wang, Min, Shen, Tao, Spectroscopic studies of thiocyanate in silver hydrosol and the influence of halid ions, 1999, Spectrochimica Acta Part A, 55, 991-998.*

(Continued)

*Primary Examiner* — Keith Hendricks
*Assistant Examiner* — Bach Dinh
(74) *Attorney, Agent, or Firm* — Edward J. Baba; Bozicevic, Field & Francis LLP

(57) ABSTRACT

A method for determining the presence or amount of a metal-labelled analyte (12) in a sample is described. The method comprises the steps of adding a release agent (20) to the metal labelled analyte (12) to release the metal label (18) from the analyte (12), the release agent (20) forming a charged stable species (22) with the metal label (18), applying a potential to bring the charged stable species (22) to an electrode (22), dissolving the charged stable species (22) under a positive potential to form metal ions (26), and carrying out a quantitative determination procedure such as anodic stripping voltammetry to determine the presence or amount of the metal-labelled analyte (12).

20 Claims, 15 Drawing Sheets

U.S. PATENT DOCUMENTS

| | | | |
|---|---|---|---|
| 7,226,562 B2 | 6/2007 | Holl et al. | |
| 2002/0137218 A1 | 9/2002 | Mian et al. | |
| 2003/0186274 A1* | 10/2003 | Limoges et al. | 435/6 |
| 2004/0058457 A1 | 3/2004 | Huang et al. | |
| 2004/0248093 A1 | 12/2004 | Coombs et al. | |
| 2005/0230713 A1 | 10/2005 | Brousseau, III | |
| 2006/0228814 A1 | 10/2006 | Linoges et al. | |
| 2006/0263818 A1 | 11/2006 | Scherer et al. | |
| 2006/0270049 A1 | 11/2006 | Todd | |
| 2007/0148039 A1 | 6/2007 | Padmanabhan et al. | |
| 2010/0034742 A1 | 2/2010 | Schwartz et al. | |
| 2011/0124008 A1 | 5/2011 | Nam et al. | |

FOREIGN PATENT DOCUMENTS

| | | |
|---|---|---|
| WO | 9002938 | 3/1990 |
| WO | 9828623 | 7/1998 |
| WO | 9853301 | 11/1998 |
| WO | 9938612 | 8/1999 |
| WO | 0013014 | 3/2000 |
| WO | 0025136 | 5/2000 |
| WO | 0167079 | 9/2001 |
| WO | 2004016160 | 2/2004 |
| WO | 2004020112 | 3/2004 |
| WO | 2004113919 | 12/2004 |
| WO | 2005046437 | 5/2005 |
| WO | 2005121792 | 12/2005 |
| WO | 2006065762 | 6/2006 |
| WO | 2006118420 | 11/2006 |
| WO | 2008002462 | 1/2008 |
| WO | 2008074146 | 6/2008 |

OTHER PUBLICATIONS

Yang, Pinghua, Wei, Wanzhi, Tao, Chunyuan, Determination of trace thiocyanate with nano-silver coated multi-walled carbon nanotubes modified glassy carbon electrode, 2007, Analytica Chimica Acta, 585, 331-336.*

Dequaire, et al. (2000) "An Electrochemical Metalloimmunoassay Based on a Colloidal Gold Label" Anal. Chem. 72:5521-5528.

Guo and Wang, "Synthesis and electrochemical applications of gold nanoparticles," Analytica Chimica Acta 598, 181-92 (2007).

Fritzsche and Taton, "Metal nanoparticles as labels for heterogeneous, chip-based DNA detection," Nanotechnology 14, R63-R73 (2003).

Kim et al., "Superparamagnetic Nanoparticle-Based Nanobiomolecular Detection in a Microfluidic Channel" Current Applied Physics, 6(6):976-981 (2006).

* cited by examiner

ELECTROCHEMICAL DETECTION OF A METAL—LABELLED ANALYTE

The present invention relates to electrochemical assays in particular such assays utilising metal nanoparticles as an electrochemical label.

Prior art assays involving metal labels, such as those described in WO 2005/121792 require chemical oxidants in order to dissolve the metal nanoparticles. A problem with this is that the oxidant can interfere with the electrochemical profile of the scan by disrupting the baseline of the scan. The assay described in WO 2005/121792 relies on the formation of metal ions in order for the metal to be transferred to an electrode surface electroanalytically. This is problematic when analysing biological samples. Proteins and other molecules in a biological sample solution typically bind to the metal ions rendering them electrochemically inactive. The metal ions can also be rendered electrochemically inactive by chelation/coupling with the chemical oxidate. Accordingly, the sensitivity of the signal is reduced.

WO 2004/016160 discloses use of a chemical redox cleavant to release an organic polymer nanoparticle from a nanoparticle-labelled analyte. Electrochemical flow cytometry is then used to detect redox products (such as metal ions) released by the redox cleavant from the polymer nanoparticle.

The present invention seeks to overcome one or more of the above problems.

According to a first aspect of the present invention there is provided a method for determining the presence or amount of a metal-labelled analyte in a sample, the method comprising the steps of: adding a release agent to the metal labelled analyte to release the metal label from the analyte, the release agent and the metal label together forming a charged species, applying a potential to bring the charged species to an electrode, applying a positive potential to the charged species to form metal ions, and carrying out quantitative determination procedure to determine the presence or amount of the metal-labelled analyte. The metal ions are formed at the electrode surface. There is therefore little opportunity for the metal ion to be deactivated before it is measured. It is therefore not necessary to form a complex between the metal ion and a chelating agent. Moreover, as an electrochemical potential is used to dissolve the metal label, it is not necessary to use a chemical oxidant and the problems associated with chemical oxidants are avoided.

The charged species is typically insoluble.

Typically, the release agent includes a charged component, the charged component of the release agent and the metal nanoparticle together forming the charged species.

The charged species may be brought to an electrode by applying a positive potential, which also results in the formation of the metal ions.

The charged species is preferably negatively charged, although in some embodiments it may be positively charged.

The release agent may be any salt or chemical that is able to form a charged layer on the surface of the metal label and thus enable it to be moved under an electrical potential.

The release agent may comprise a thiol with a charged unit. The thiol acts to denature or destroy the binding between the metal label and the analyte. The charged unit provides a charge to the metal label.

Examples of suitable release agents include ammonium thiocyanate and potassium thiocyanate. Instead of thiocyanate, the release agent may comprise thiosulphate or a charged thiol chain. The release agent may provide ions to form the charged species. For example, suitable release agents include NaCl or HCl, which are able to provide chloride ions to form the charged species. NaCl and HCl are particularly useful as release agents because they do not form a complex with the metal ions after oxidation.

The release agent is preferably in a concentration of about 1M or more. This range is preferred as below this molarity the silver sensitivity is not as good.

The method may further include labelling the analyte with the metal label wherein the analyte is incubated with a binding moiety capable of binding to the analyte and which is labelled with the metal label. The analyte may be incubated with a further binding moiety capable of binding to the analyte and which is secured to a solid support. The solid support may be mobile or fixed, it may be magnetised, it may be a particle that may be larger or smaller than the metal nanoparticle so as to allow filtering of unbound from bound metal nanoparticles, it may be a charged particle in order to enable electrical separation, it may be a porous structure, it may be a two- or three-dimensional surface or structure.

In a preferred embodiment the metal label is silver or gold, for example a silver nanoparticle or a gold nanoparticle. Preferably the metal label is a particulate or a nanoparticle label such as a silver nanoparticle.

The analyte can be labelled indirectly wherein the label is attached to a species or binding moiety which is in turn bound to the analyte.

The quantitative determination procedure may be a voltammetric method, such as anodic stripping voltammetry (ASV).

Preferred embodiments will now be described by way of example only and with reference to the drawings in which:

FIG. 1 schematically illustrates an embodiment of the invention;

Figure 15:
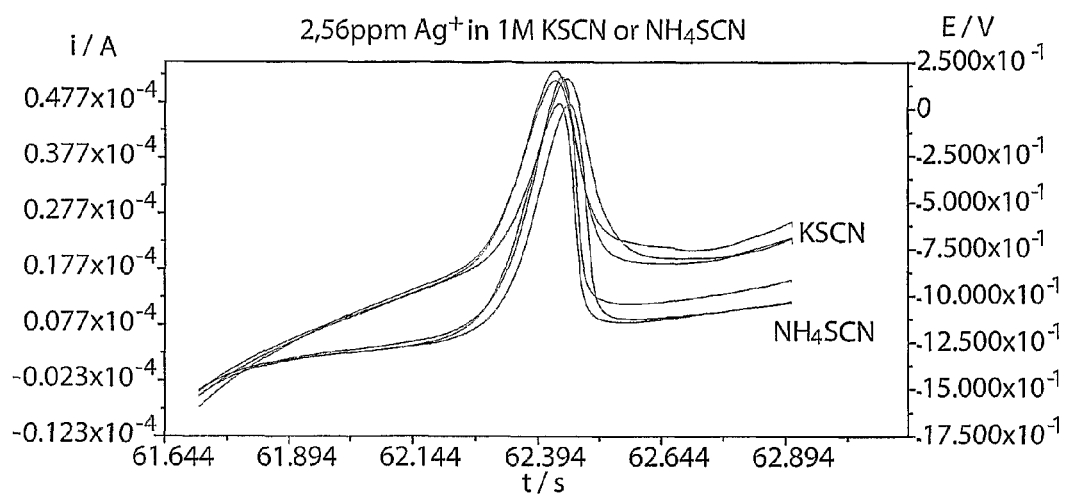
Figure 16:
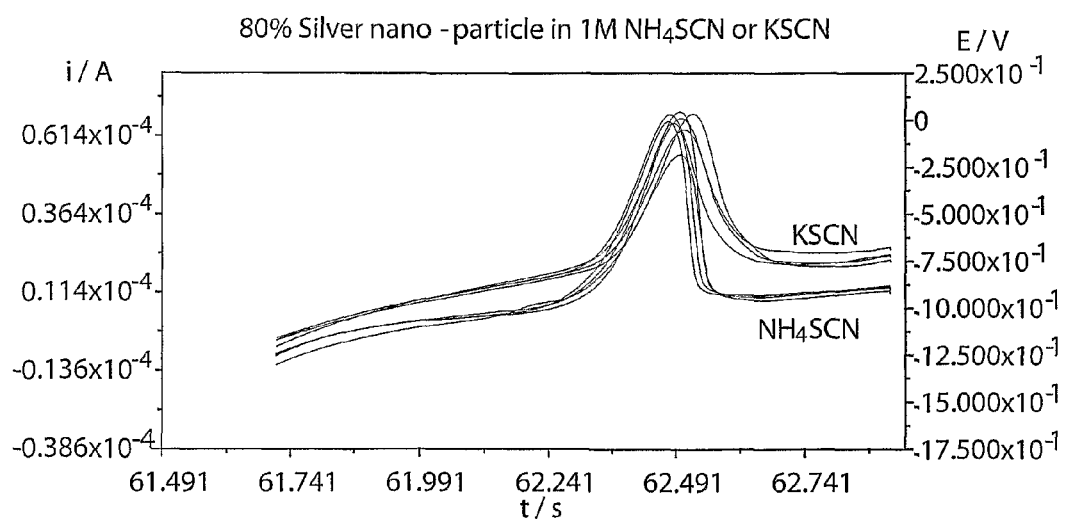
Figure 17:
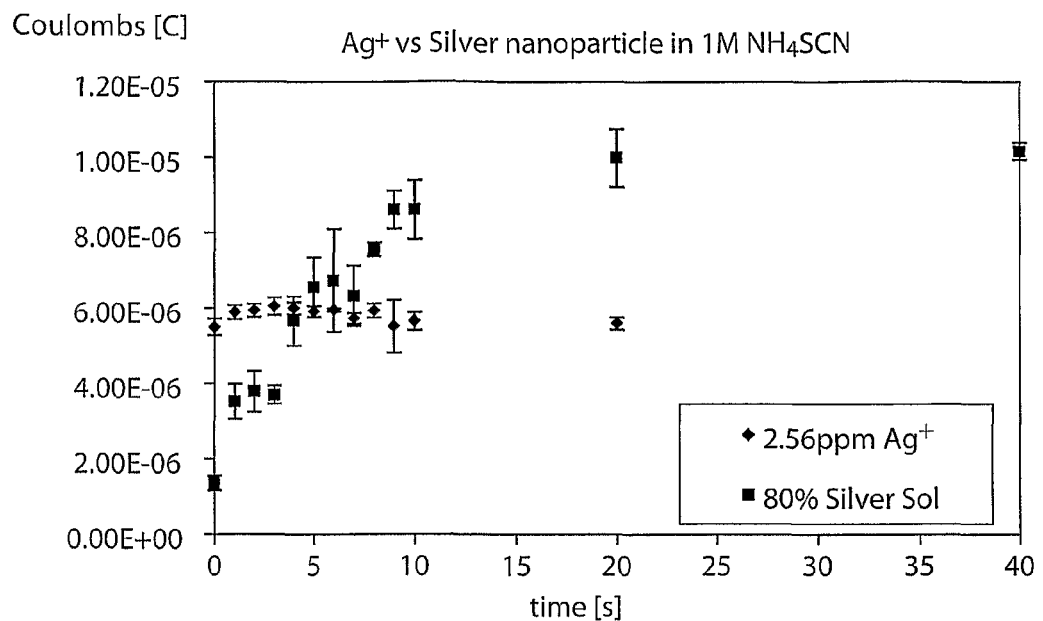
Figure 18:
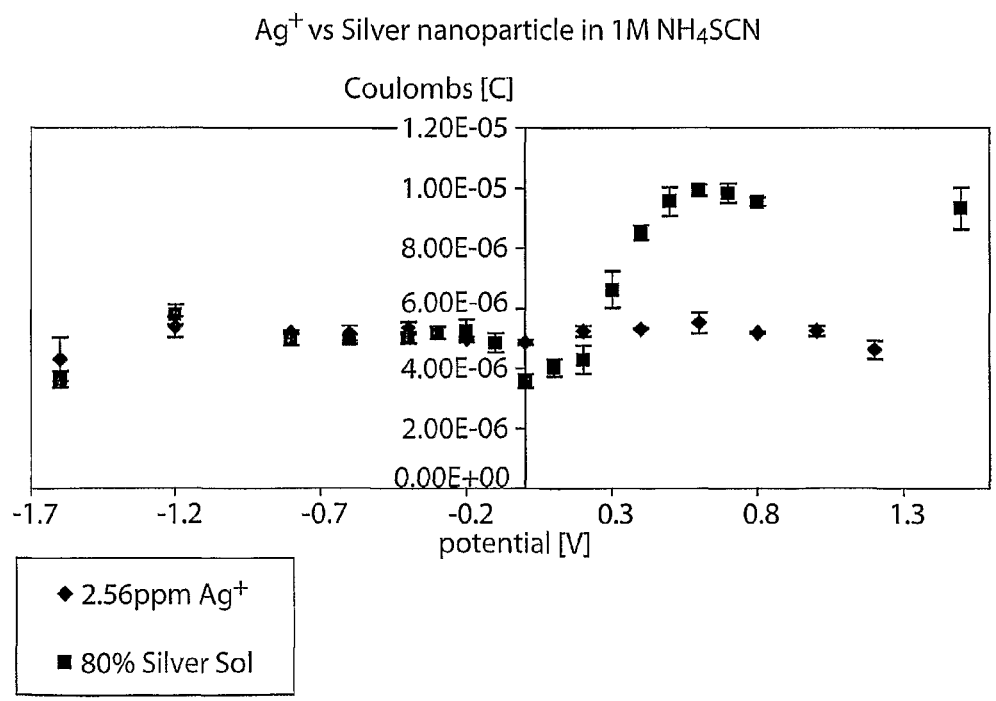
Figure 19:
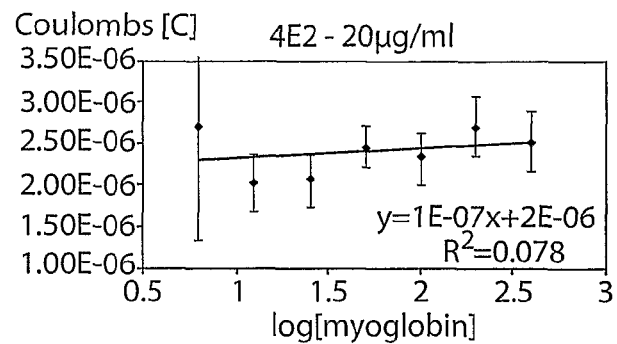
Figure 19:
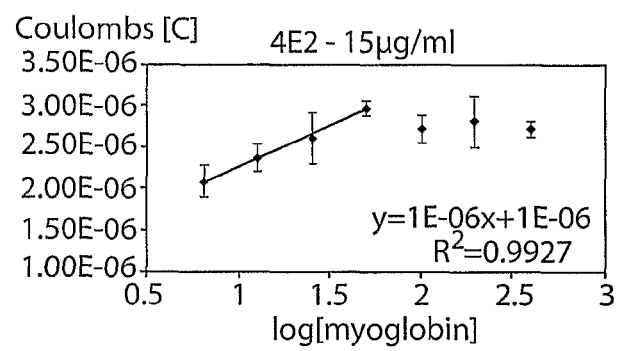
Figure 19:
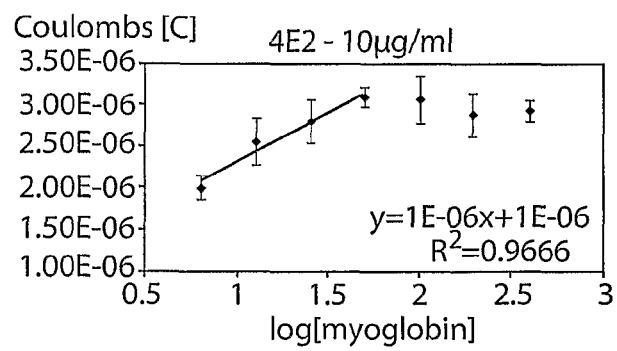
Figure 19:
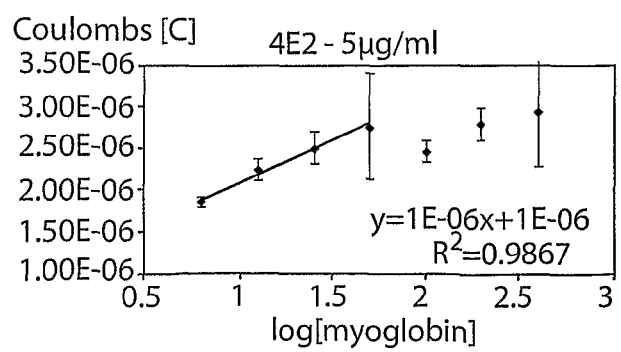

FIGS. 14a to f show the effect of 80% and 100% silver nanoparticle solution on size distribution;

FIGS. 15 and 16 compare results with KSCN and $NH_4SCN$;

FIGS. 17 and 18 compare the influence of pre-treatment time on an embodiment of the method;

FIG. 19 shows results for assays for myoglobin to determine the amount of antibody required for maximum sensitivity of the assay;

FIGS. 20 to 23 show the results for further embodiments of the method; and

Figure 24:
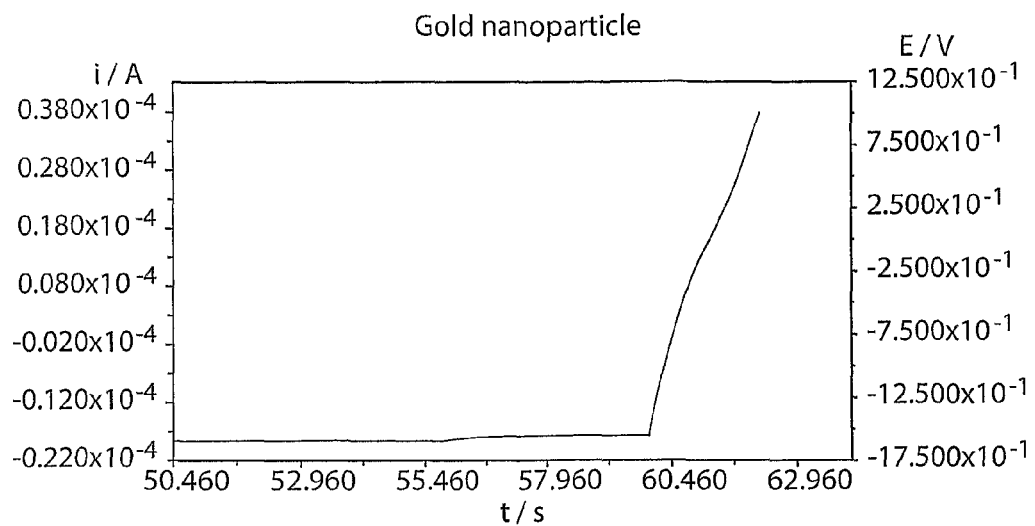
Figure 25:
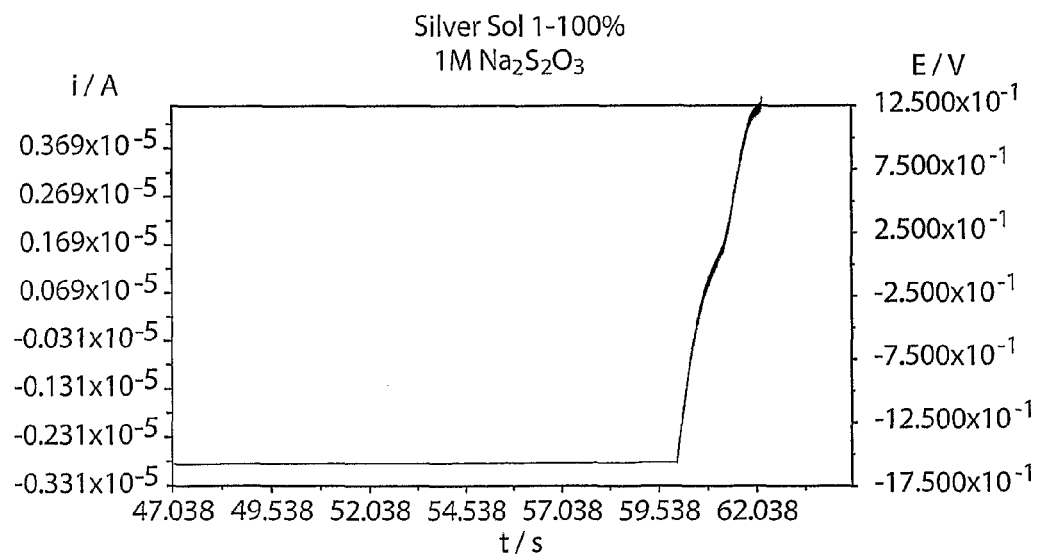

FIGS. 24 and 25 illustrate negative results where the measured species is uncharged.

Figure 1:
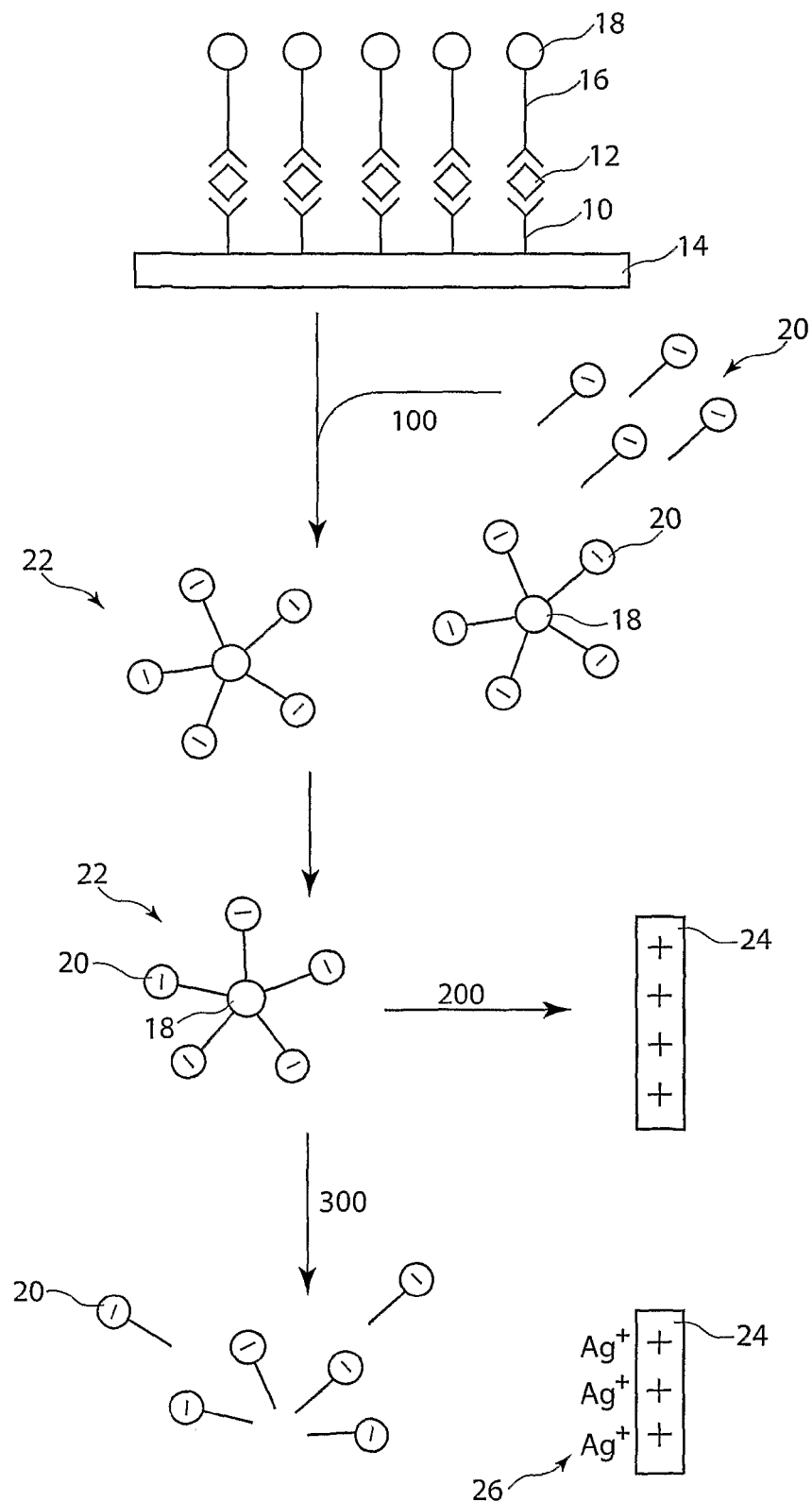

The assay determines the presence or amount of an analyte of interest (such as an antibody, a mimotope or a nucleic acid strand) and one embodiment is schematically illustrated in FIG. 1. In a preferred embodiment, a first binding moiety 10 which is capable of binding to an analyte 12 of interest is attached to a solid phase 14 (surface or magnetic particle). A second binding moiety 16 which is capable of binding to a different region on the analyte 12 is labelled with a metal label 18, typically a particulate label.

A sample solution comprising the analyte 12 is added to the solid support 14. The analyte 12 binds to the first binding moiety 10. The support 14 is then incubated with a solution comprising the labelled second binding moiety 16, which binds to the analyte 12. In effect a "sandwich" occurs between the substrate and the silver particle 18 thus capturing the particle 18. Unbound particles are then removed (such as by washing). This ensures such particles are not oxidised.

In a preferred embodiment, silver nanoparticles 18 are used as an electrochemical label. The silver nanoparticle 18 gives a molecular amplification of the electrochemical signal, as each 40 nm silver nanoparticle contains approximately $10^6$ silver ions. Thus the sensitivity of the assay is enhanced. In addition, silver is preferred as it forms stable nanoparticles which can be used as a bio-nanolabel 18. Furthermore, silver nanoparticles 18 are easily oxidised electrically to form silver ions. Some other metal nanoparticles require harsh chemical oxidants to form metal ions.

In a preferred embodiment, ammonium thiocyanate 20 is introduced 100 and removes the silver nanoparticle 18 from its biocomplex and forms a layer (which may be a monolayer) chemically bound around the silver nanoparticle resulting in a negatively charged nanoparticle 22. The charged nanoparticle 22 can be migrated 200 under an electrical potential to the surface of a positive electrode. The silver nanoparticle at that electrode then dissolves under the positive potential 300 to form silver ions 26. The silver ions 26 are then measured by accumulation stripping voltammetry. A small proportion of the silver ions 26 may be in the form of a complex with a chelating agent where the release agent is capable of chelating the silver ions.

Other release agents 20 (such as a thiol with a charged unit, for example thiosulphate) may be used. Non-thiolate molecules such as NaCl and HCl could also be used.

COMPARATIVE EXAMPLE 1

This Comparative Example explains the chemistry behind the formation of the electroactive complexes measured in the method disclosed in WO 2005/121792.

1. Measurements of Complexed of Silver Ions ($Ag^+$)

Silver ions in the presence of $NH_4SCN$ form strong electroactive complexes:

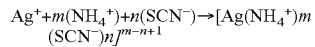

Those complexes can be electrochemically measured using ASV. In this process silver complexes at negative potential are first deposited on the surface of carbon paste electrode:

Then the potential is changed to positive value and silver complexes are stripped off the electrode giving a peak in the current.

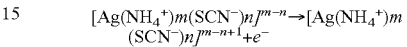

Ammonium thiocyanate also forms complexes with other metal ions and the ammonium thiocyanate positions the electrochemistry of these metal ions away from the electrochemistry of the silver ions complex thus removing spectroscopic interference.

Standard solutions of $AgNO_3$ were prepared (1.25, 6.25, 12.5, 25, 37.5, 50 and 62.5 ppm $AgNO_3$). To each 160 μl of standard solution, 40 μl of 5M $NH_4SCN$ were added. Subsequently, 50 μl of each of the $AgNO_3$ and $NH_4SCN$ solutions were, in turn, applied onto an electrode and ASV conducted. The ASV parameters were as follows:
 a) +0.4V for 10 s (pre-treatment)
 b) linear sweep +0.4V→−1.6V at scan rate=1V/s and step potential=0.005V
 c) −1.6V for 5 s
 d) −1.2 V for 55 s
 e) linear sweep−1.2V→+0.1V at scan rate=1V/s and step potential=0.01V
2) Between Each Measurement the Electrode was Cleaned with 5M $NH_4SCN$ and Running ASV and then Wiping with Tissue.

TABLE 1

| | Ag+ [ppm] | | | | | | |
|---|---|---|---|---|---|---|---|
| | 1 | 5 | 10 | 20 | 30 | 40 | 50 |
| 1 | 4.40E−07 | 2.48E−06 | 5.34E−06 | 1.03E−05 | 1.39E−05 | 1.68E−05 | 2.34E−05 |
| 2 | 4.23E−07 | 2.48E−06 | 4.86E−06 | 9.73E−06 | 1.62E−05 | 1.69E−05 | 2.10E−05 |
| 3 | 3.91E−07 | 2.51E−06 | 4.73E−06 | 1.07E−05 | 1.45E−05 | 1.77E−05 | 1.96E−05 |
| Mean | 4.18E−07 | 2.49E−06 | 4.97E−06 | 1.02E−05 | 1.49E−05 | 1.71E−05 | 2.13E−05 |
| St. Dev. | 2.48E−08 | 1.94E−08 | 3.19E−07 | 4.8E−07 | 1.21E−06 | 4.61E−07 | 1.91E−06 |
| CV % | 5.93 | 0.78 | 6.42 | 4.69 | 8.17 | 2.69 | 8.96 |

Figure 2:
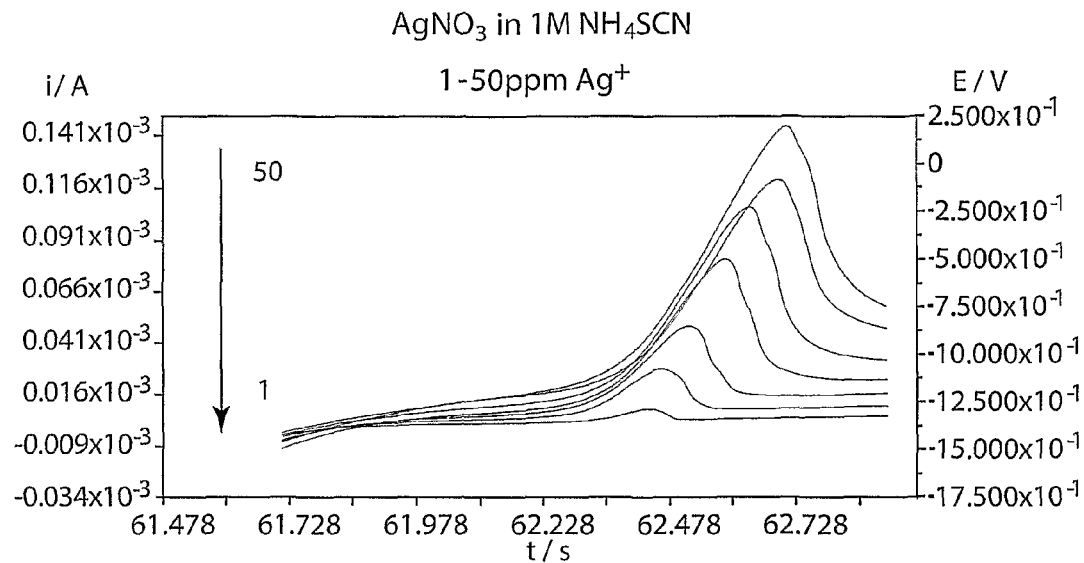
FIGS. 2 and 3 show the anodic stripping voltammetry (ASV) scan results for standard solutions of $AgNO_3$ plus 1M $NH_4SCN$ (1-50 ppm $Ag^+$)
Figure 3:
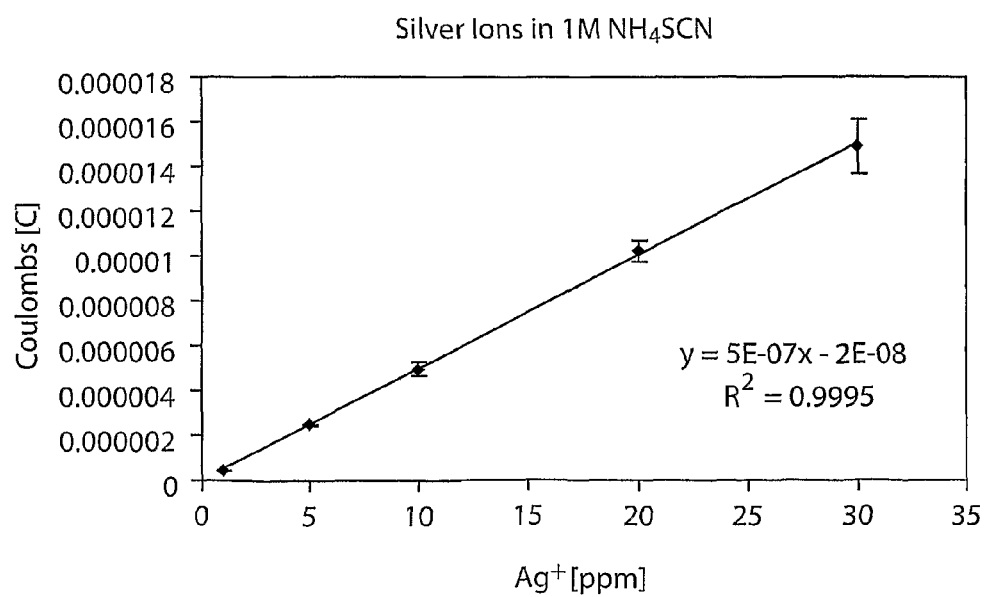

The results are displayed in FIGS. 2 and 3. The area under the peak is proportional to the concentration of $Ag^+$ in the range 1 to 50 ppm.

COMPARATIVE EXAMPLE 2

The same experiment was carried out using lower concentrations of $Ag^+$.

TABLE 2

| | Ag+ [ppm] | | | | | | |
|---|---|---|---|---|---|---|---|
| | 0.01 | 0.025 | 0.05 | 0.1 | 0.25 | 0.5 | 0.8 |
| 1 | no peak | no peak | no peak | 1.2E−08 | 6.4E−08 | 1.6E−07 | 2.7E−07 |
| 2 | no peak | no peak | no peak | 1.7E−08 | 6.4E−08 | 1.5E−07 | 2.5E−07 |
| 3 | no peak | no peak | no peak | 5.1E−09 | 5.4E−08 | 1.5E−07 | 2.4E−07 |

TABLE 2-continued

| | Ag+ [ppm] | | | | | | |
|---|---|---|---|---|---|---|---|
| | 0.01 | 0.025 | 0.05 | 0.1 | 0.25 | 0.5 | 0.8 |
| Mean | #DIV/0! | #DIV/0! | #DIV/0! | 1.1E−08 | 6.1E−08 | 1.5E−07 | 2.5E−07 |
| St. Dev. | #DIV/0! | #DIV/0! | #DIV/0! | 5.7E−09 | 5.9E−09 | 7.0E−09 | 1.2E−08 |
| CV % | #DIV/0! | #DIV/0! | #DIV/0! | 51.62 | 9.76 | 4.59 | 4.83 |

Figure 4:
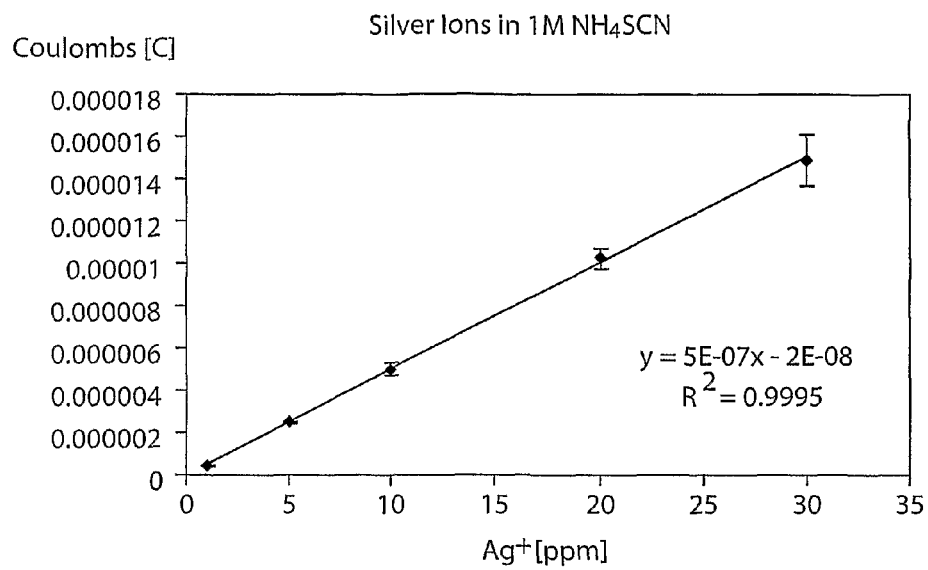
FIGS. 4 and 5 show the anodic stripping voltammetry (ASV) scan results for standard solutions of $AgNO_3$ plus 1M $NH_4SCN$ (0.01-0.8 ppm $Ag^+$)
Figure 5:
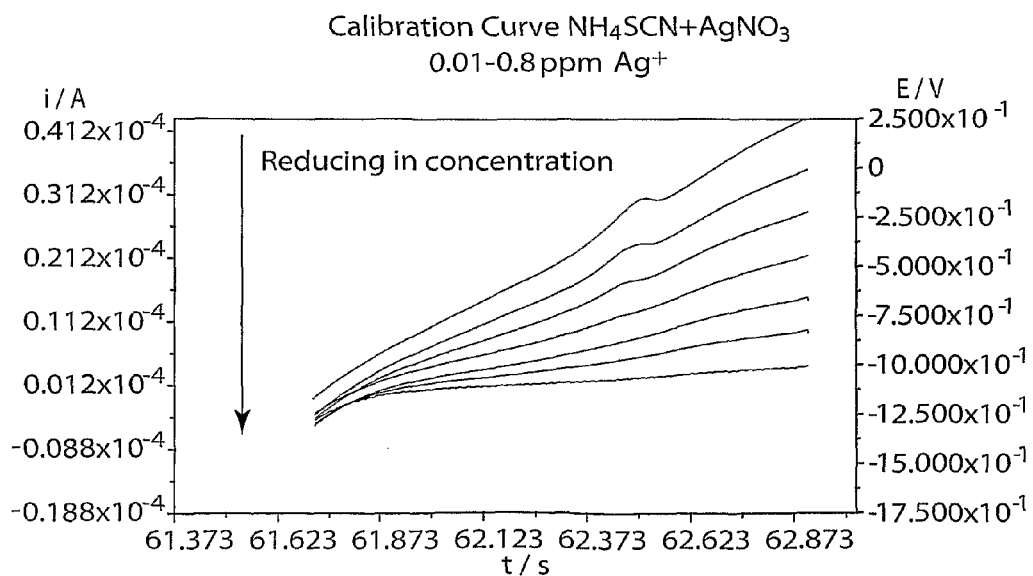
Figure 6:
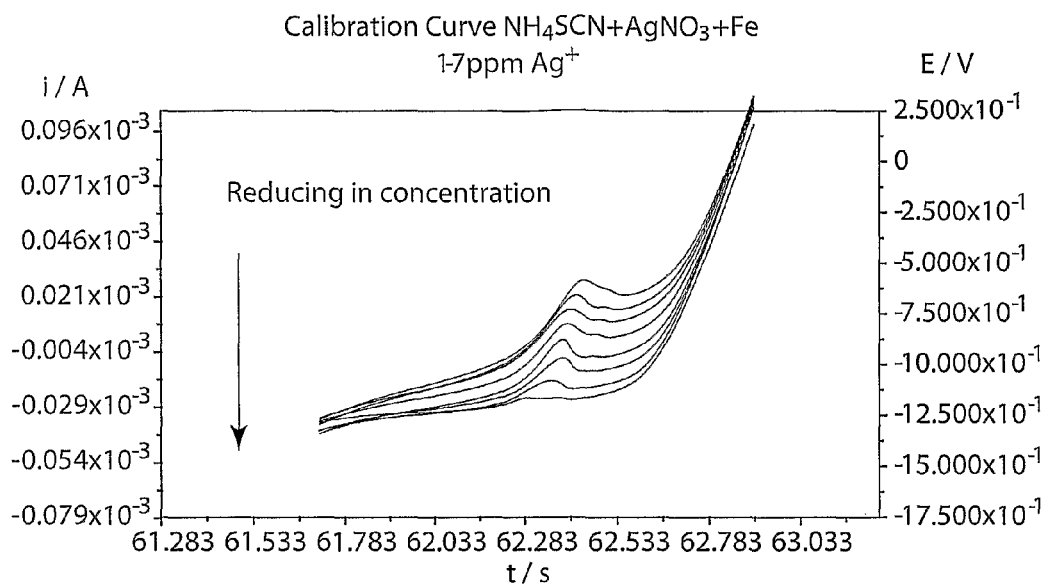
FIGS. 6 and 7 shows the concentration of $Ag^+$ in the presence of an oxidant ferricyanide.
Figure 7:
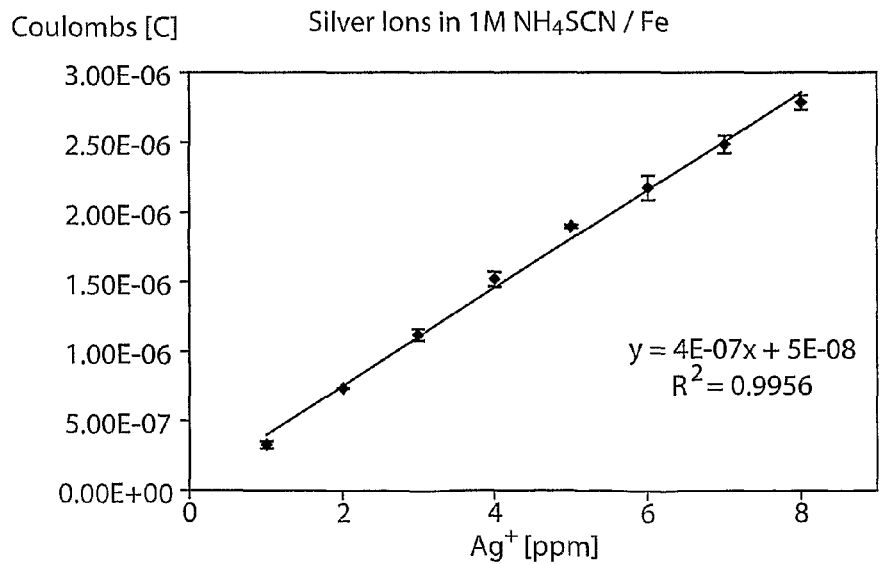
Figure 8:
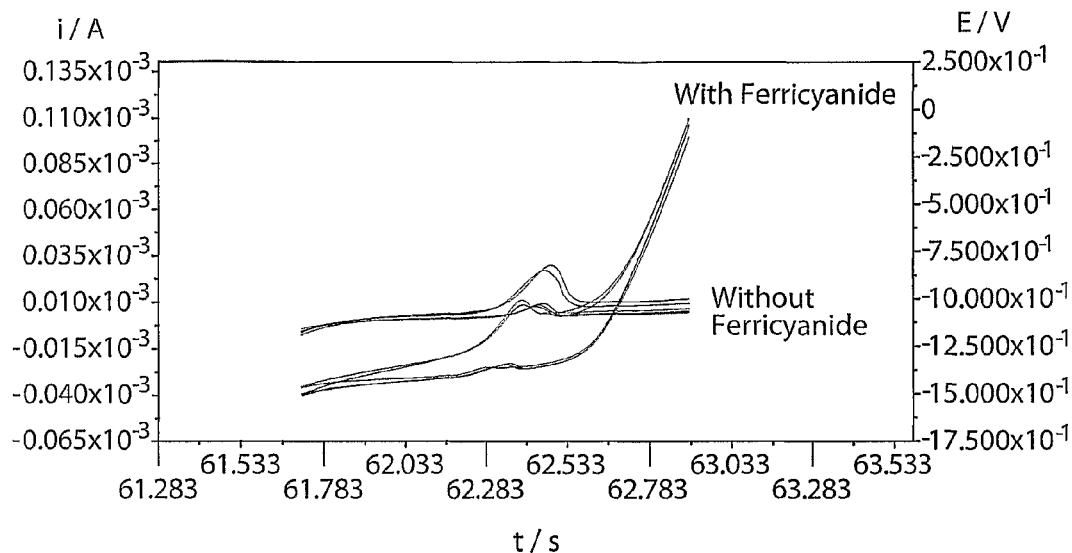
FIGS. 8 to 11 show the concentration of $Ag^+$ in the presence/absence of ferricyanide.
Figure 9:
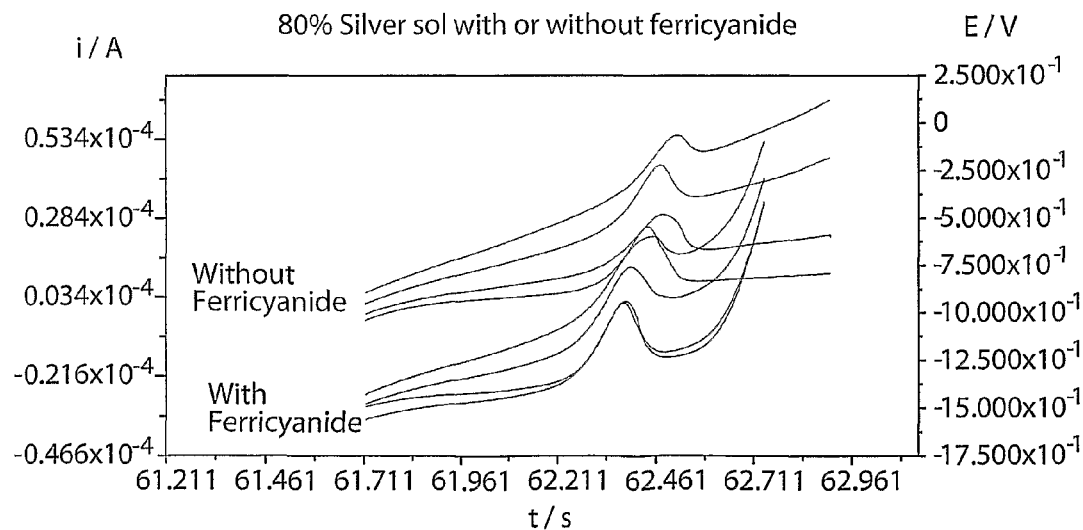

The results are displayed in FIGS. 4 and 5.

COMPARATIVE EXAMPLE 3

Prior art assays, such as described in WO 2005/121792 use an oxidant (ferricyanate) to form silver ions for use in the methodology described in Examples 1 and 2. The following measurements were conducted in the presence of 0.05M $K_3Fe(CN)_6$ and 0.01M $K_4Fe(CN)_6$

TABLE 3

| | Ag+ [ppm] | | | | | | | |
|---|---|---|---|---|---|---|---|---|
| | 1 | 2 | 3 | 4 | 5 | 6 | 7 | 8 |
| 1 | 3.39E−07 | 7.31E−07 | 1.13E−06 | 1.57E−06 | 1.90E−06 | 2.07E−06 | 2.41E−06 | 2.73E−06 |
| 2 | 3.45E−07 | 7.34E−07 | 1.07E−06 | 1.50E−06 | 1.89E−06 | 2.20E−06 | 2.52E−06 | 2.79E−06 |
| 3 | 2.99E−07 | 7.34E−07 | 1.14E−06 | 1.47E−06 | 1.88E−06 | 2.23E−06 | 2.52E−06 | 2.83E−06 |
| Mean | 3.28E−07 | 7.33E−07 | 1.12E−06 | 1.51E−06 | 1.89E−06 | 2.17E−06 | 2.48E−06 | 2.78E−06 |
| St. Dev. | 2.5E−08 | 1.65E−09 | 4.07E−08 | 5.26E−08 | 1.37E−08 | 8.83E−08 | 6.36E−08 | 5.17E−08 |
| CV % | 7.633131 | 0.225412 | 3.650072 | 3.47912 | 0.722371 | 4.074576 | 2.562306 | 1.859349 |

The results obtained are displayed in FIGS. 6 to 9. Whilst, the calibration curve for silver ions with and without ferricyanide is very similar, the shape of the scan results is different.

The following Examples illustrate the subject matter of preferred embodiments of the present invention.

EXAMPLE 4

Electrochemical Behaviour of Silver Nanoparticles with or without Ferricyanide A 'mix' solution of 5M $NH_4SCN$, 0.25M $K_3Fe(CN)_6$ and 0.05M $K_4Fe(CN)_6$ was prepared. Two solutions of 160 μl silver nanoparticles were prepared. 40 μl of 5M $NH_4SCN$ were added to the first silver solution. 40 μl of the mix solution were added to the second solution. Once prepared, 50 μl of each solution were added in turn onto an electrode and ASV conducted.

TABLE 4

| Silver Nanoparticles | No Fe | +Fe |
|---|---|---|
| 1 | 2.23E−06 | 2.36E−06 |
| 2 | 2.06E−06 | 2.28E−06 |
| 3 | 1.93E−06 | 2.15E−06 |
| 4 | 1.37E−06 | 1.88E−06 |

TABLE 4-continued

| Silver Nanoparticles | No Fe | +Fe |
|---|---|---|
| Mean | 1.9E−06 | 2.17E−06 |
| St. Dev | 3.72E−07 | 2.12E−07 |
| CV % | 19.60653 | 9.807044 |

Figure 10:
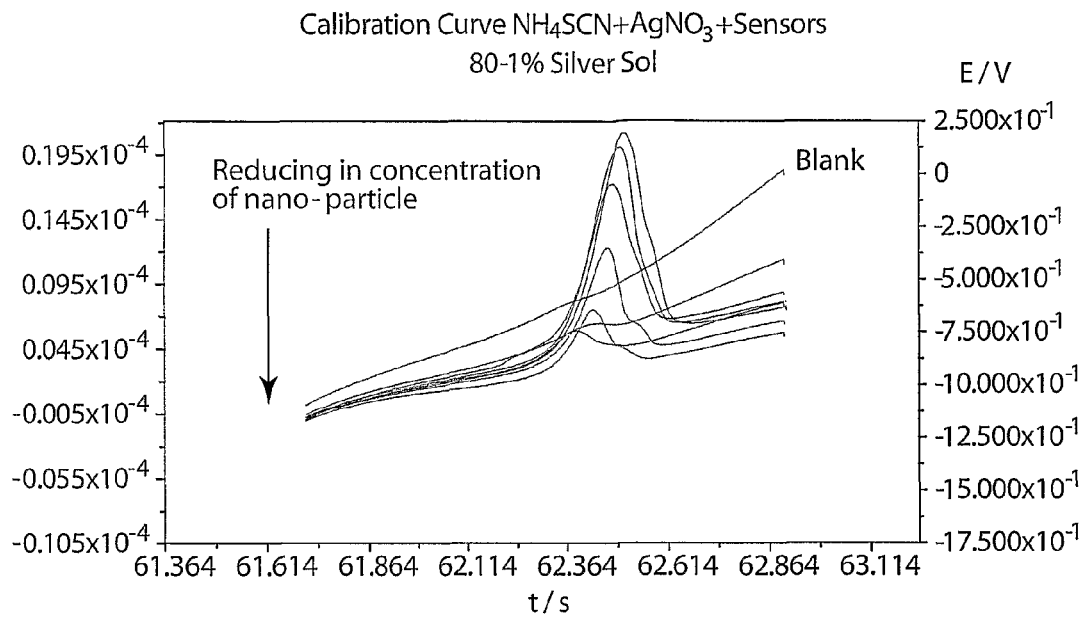

The results are shown in FIG. 10. Silver nanoparticles in the presence of thiocyanate generates similar but stronger peaks to the peaks generated by silver nanoparticles with the ferricyanide oxidant. However, the baseline is better in the case of silver nanoparticles without ferricyanide oxidant. The baseline is flatter and there is no current rise after the stripping peak (as in the case of the ferricyanide). Peak finding and integration or height determination are thus easier.

What is more (as shown in the next experiment) the area under the peak is proportional to silver nanoparticle concentration:

TABLE 5

| | Nanoparticle [%] | | | | | | | |
|---|---|---|---|---|---|---|---|---|
| | 1 | 4 | 8 | 16 | 32 | 48 | 64 | 80 |
| 1 | no peak | 1.19E−07 | 2.66E−07 | 5.21E−07 | 9.99E−07 | 1.70E−06 | 2.10E−06 | 2.42E−06 |
| 2 | no peak | 1.18E−07 | 2.07E−07 | 4.31E−07 | 9.57E−07 | 1.51E−06 | 1.88E−06 | 2.66E−06 |
| 3 | no peak | 8.77E−08 | 2.14E−07 | 4.23E−07 | 9.25E−07 | 1.44E−06 | 1.95E−06 | 2.31E−06 |
| 4 | no peak | 6.31E−08 | 1.81E−07 | 4.10E−07 | 8.49E−07 | 1.29E−06 | 1.75E−06 | 2.21E−06 |
| Mean | #DIV/0! | 9.70E−08 | 2.17E−07 | 4.46E−07 | 9.32E−07 | 1.49E−06 | 1.92E−06 | 2.40E−06 |
| St. Dev. | #DIV/0! | 2.69E−08 | 3.54E−08 | 5.08E−08 | 6.32E−08 | 1.7E−07 | 1.46E−07 | 1.93E−07 |
| CV % | #DIV/0! | 27.77 | 16.32 | 11.40 | 6.78 | 11.41 | 7.58 | 8.04 |

Figure 11:
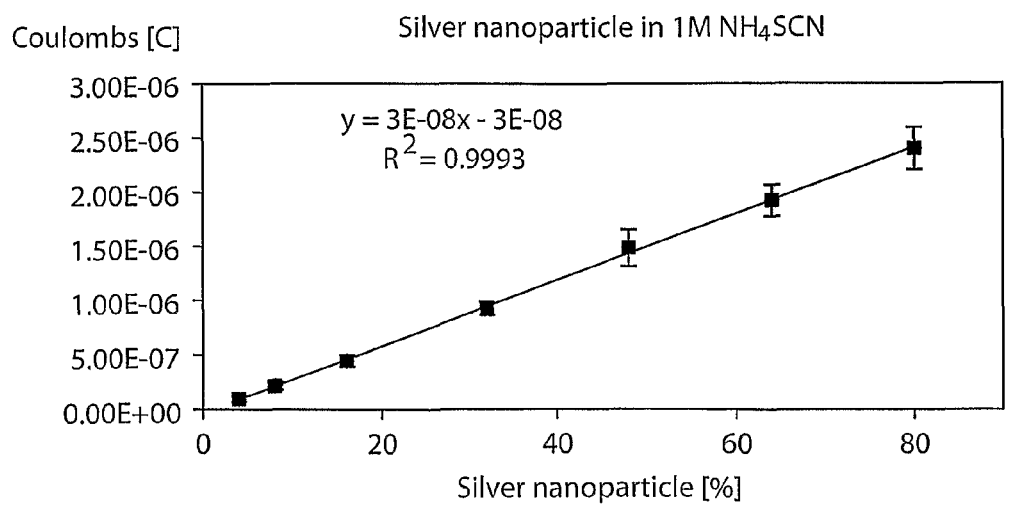

These data are displayed in FIG. 11.

EXAMPLE 5

To check whether $NH_4SCN$ dissolves silver nanoparticle, spectroscopic methods can be used. The absorbance of silver nanoparticle with and without NH$_4$SCN can be measured from 500 to 300 nm.

Silver nanoparticle (40 nm) has an absorption peak at around 400 nm and we can see that after adding NH$_4$SCN this peak vanishes. It may mean that silver nanoparticle dissolves but according to literature the mechanism of vanishing of this peak is different: SCN$^-$ is coupled to the surface of silver particles as a monolayer and silver nanoparticles form aggregates. This is why absorbance of silver nanoparticle at 400 nm decreases but a new absorbance peak is obtained at around 550 nm, so the experiment was repeated with a wider range of wavelengths.

Figure 12:
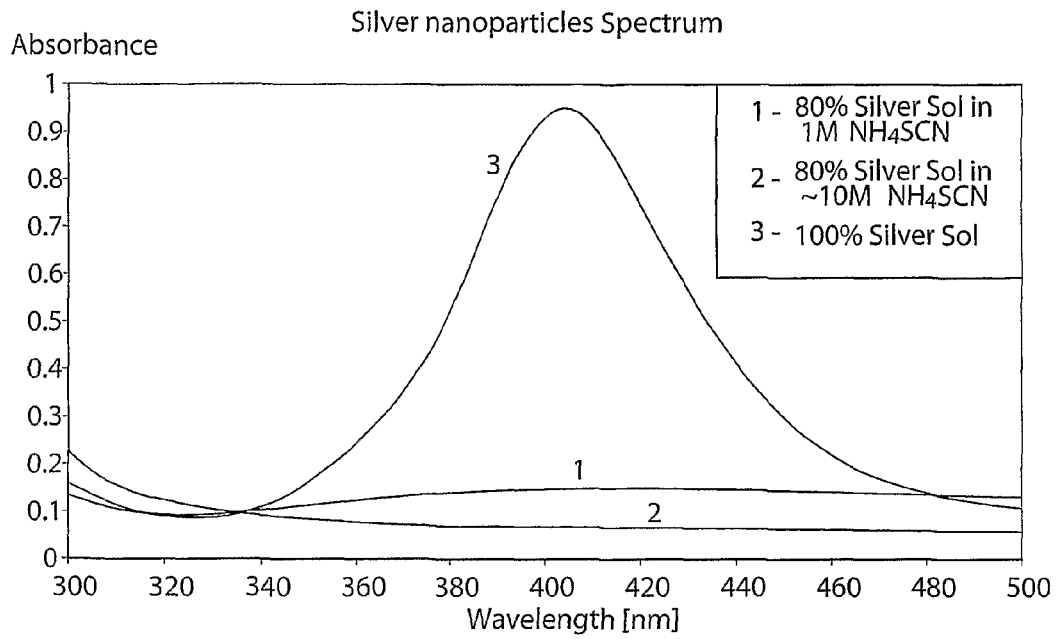
FIGS. 12 and 13 show the absorbance of silver nanoparticle with and without $NH_4SCN$.
Figure 13:
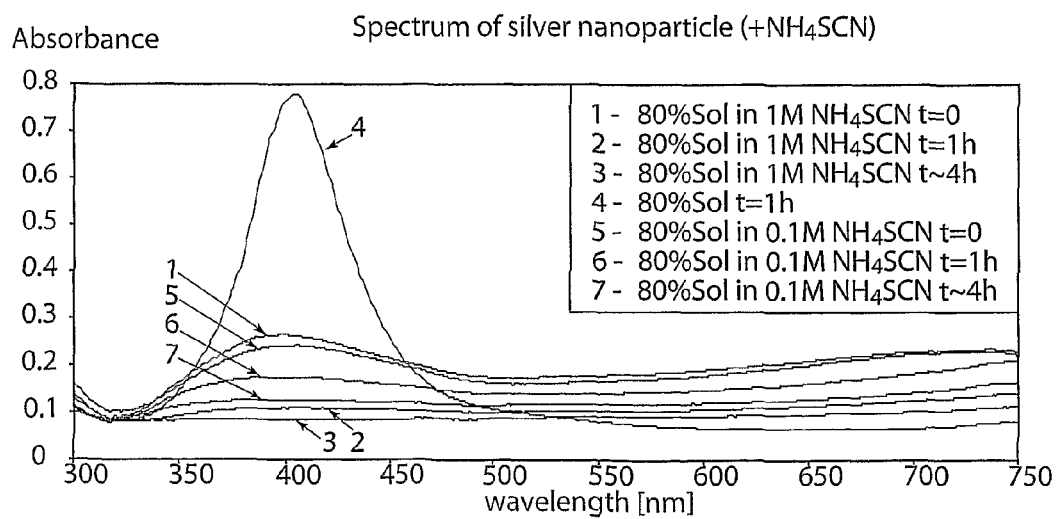

These data are displayed in FIGS. 12 and 13.

The UV spectrum shows a decrease in signal at 400 nm and a broad peak increase in signal at around 650 nm indicating an increase in size of the nanoparticle.

EXAMPLE 6

Figure 14A:
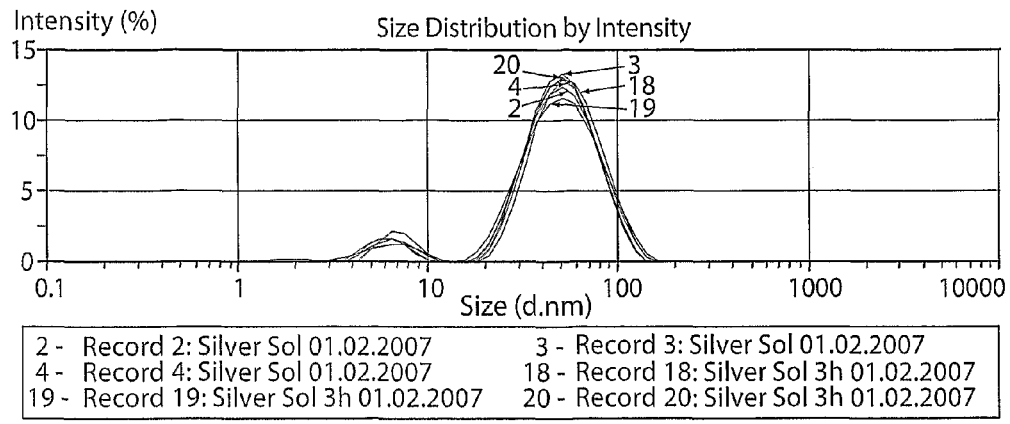

In this experiment, the size of silver particles in 100% silver nanoparticle solution and in 80% silver nanoparticle solution with 1M NH$_4$SCN (filtered) was measured using Malvern zeta-sizer instrument. FIG. 14*a* shows the results for a 100% silver nanoparticle solution. The measurements were taken at t=0 and a further three measurements were taken at t=3 hours.

Figure 14B:
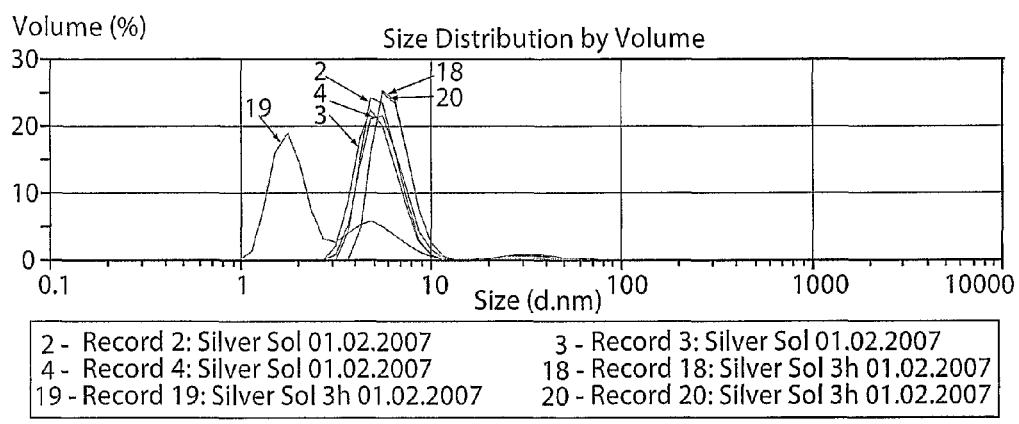
Figure 14C:
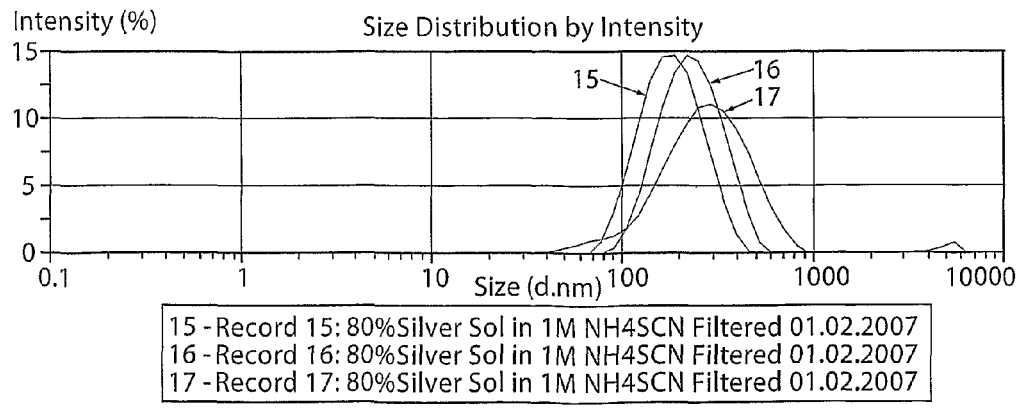
Figure 14D:
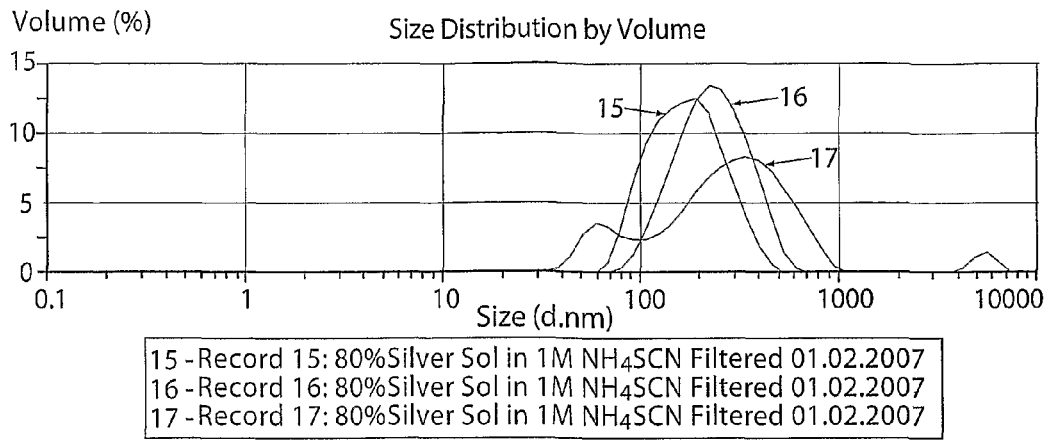

The measurements of silver nanoparticle solution show that the silver nanoparticle is stable in solution. This is shown in FIG. 14*b*. After adding NH$_4$SCN the size of silver nanoparticles changes as shown in FIG. 14*c*. After the ammonium thiocyanate was added it can be clearly seen from the results that the particles have aggregated and not dissolved at all (see FIG. 14*d*).

Figure 14E:
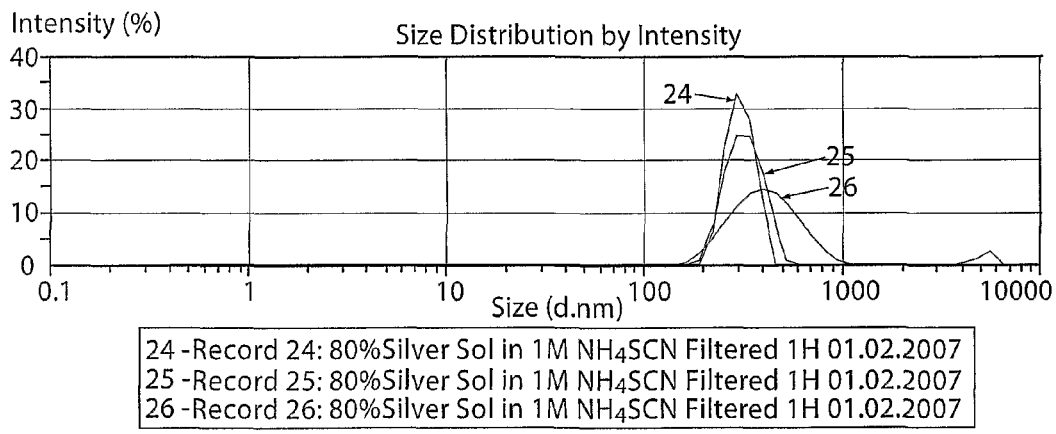
Figure 14F:
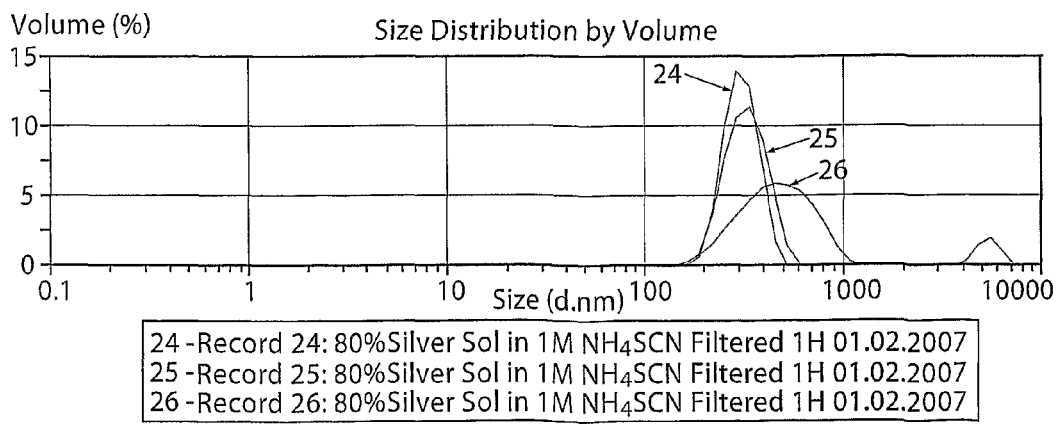

After one hour, the size of aggregates seems to be growing (see FIGS. 14*e* and *f*).

EXAMPLE 7

The indication from the data is that the ammonium thiocyanate forms a thiocyanate monolayer around the silver nanoparticle. Similar results can be obtained by changing the molecule but retaining the thiocyanate unit. In this experiment the measurement of silver nanoparticle and silver ions was prepared with NH$_4$SCN as well as with KSCN:

TABLE 6

| | 2.56 ppm Ag+ | | 80% Silver Nanoparticle | |
|---|---|---|---|---|
| n | 1M KSCN | 1M NH4SCN | 1M KSCN | 1M NH4SCN |
| 1 | 4.51E−06 | 4.78E−06 | 3.64E−06 | 8.24E−06 |
| 2 | 5.10E−06 | 5.01E−06 | 7.69E−06 | 5.10E−06 |
| 3 | 5.62E−06 | 5.09E−06 | 4.94E−06 | 4.78E−06 |
| 4 | 5.78E−06 | 5.09E−06 | 7.89E−06 | 3.14E−06 |
| 5 | 5.34E−06 | 5.06E−06 | 9.84E−06 | 5.78E−06 |
| 6 | 7.05E−06 | 5.12E−06 | 7.85E−06 | 6.82E−06 |
| 7 | 5.04E−06 | 4.94E−06 | 8.09E−06 | 4.79E−06 |
| 8 | 5.39E−06 | 4.57E−06 | 7.93E−06 | 7.90E−06 |
| 9 | 5.27E−06 | 4.78E−06 | 6.79E−06 | 7.32E−06 |
| 10 | 5.64E−06 | 5.19E−06 | 9.88E−06 | 7.71E−06 |
| Mean | 5.47E−06 | 4.96E−06 | 7.45E−06 | 6.16E−06 |
| St. Dev. | 6.64E−07 | 1.94E−07 | 1.94E−06 | 1.69E−06 |
| CV % | 12.13 | 3.90 | 26.06 | 27.43 |

The results are displayed in FIGS. 15 and 16.

We can see that KSCN also forms electroactive complexes with Ag$^+$ and with silver nanoparticle generates current peaks.

EXAMPLE 8

We have demonstrated above that the thiocyanate forms a monolayer on the surface of the silver nanoparticle to form a charged nanoparticle. This causes the nanoparticles to aggregate. The charged particle is migrated to the electrode under a positive potential. The following two experiments show how the silver nanoparticle may be measured by anodic stripping voltammetry. Firstly the influence of pre-treatment time (at U=+0.4V) on measurements of silver ions and silver nanoparticle was checked (see Table 7):

TABLE 7

| 2.56 ppm Ag+ in 1M NH4SCN | | | | | | |
|---|---|---|---|---|---|---|
| | time [s] | | | | | |
| | 0 | 1 | 2 | 3 | 4 | 5 |
| 1 | 5.25E−06 | 5.83E−06 | 5.85E−06 | 5.83E−06 | 5.85E−06 | 5.81E−06 |
| 2 | 5.67E−06 | 5.76E−06 | 6.13E−06 | 6.29E−06 | 6.18E−06 | 6.07E−06 |
| 3 | 5.57E−06 | 6.11E−06 | 5.83E−06 | 6.01E−06 | 5.95E−06 | 5.84E−06 |
| Mean | 5.49E−06 | 5.90E−06 | 5.94E−06 | 6.04E−06 | 5.99E−06 | 5.91E−06 |
| St. Dev. | 2.22E−07 | 1.86E−07 | 1.70E−07 | 2.32E−07 | 1.66E−07 | 1.45E−07 |
| CV % | 4.03624 | 3.15993 | 2.86715 | 3.84781 | 2.77693 | 2.45108 |

| | time [s] | | | | | |
|---|---|---|---|---|---|---|
| | 6 | 7 | 8 | 9 | 10 | 20 |
| 1 | 5.98E−06 | 5.67E−06 | 5.78E−06 | 4.69E−06 | 5.47E−06 | 5.41E−06 |
| 2 | 5.96E−06 | 5.88E−06 | 5.86E−06 | 5.91E−06 | 5.55E−06 | 5.64E−06 |
| 3 | 5.90E−06 | 5.61E−06 | 6.13E−06 | 5.91E−06 | 5.91E−06 | 5.73E−06 |
| Mean | 5.95E−06 | 5.72E−06 | 5.92E−06 | 5.50E−06 | 5.64E−06 | 5.59E−06 |
| St. Dev. | 3.82E−08 | 1.42E−07 | 1.84E−07 | 7.04E−07 | 2.37E−07 | 1.65E−07 |
| CV % | 0.64229 | 2.48712 | 3.11015 | 12.7879 | 4.2055 | 2.94536 |

| 80% Silver Nanoparticle in 1M NH4SCN | | | | | | |
|---|---|---|---|---|---|---|
| | time [s] | | | | | |
| | 0 | 1 | 2 | 3 | 4 | 5 | 6 |
| 1 | 1.16E−06 | 3.45E−06 | 4.40E−06 | 3.86E−06 | 6.32E−06 | 5.72E−06 | 5.77E−06 |
| 2 | 1.55E−06 | 3.08E−06 | 3.48E−06 | | 5.01E−06 | 6.64E−06 | 6.12E−06 |
| 3 | 1.33E−06 | 4.00E−06 | 3.46E−06 | 3.52E−06 | 5.64E−06 | 7.29E−06 | 8.29E−06 |

TABLE 7-continued

| | | | | | | | |
|---|---|---|---|---|---|---|---|
| Mean | 1.35E–06 | 3.51E–06 | 3.78E–06 | 3.69E–06 | 5.66E–06 | 6.55E–06 | 6.73E–06 |
| St. Dev. | 1.95E–07 | 4.62E–07 | 5.38E–07 | 2.37E–07 | 6.56E–07 | 7.91E–07 | 1.36E–06 |
| CV % | 14.5031 | 13.1592 | 14.2104 | 6.41866 | 11.5892 | 12.0772 | 20.2901 |

| | time [s] | | | | | |
|---|---|---|---|---|---|---|
| | 7 | 8 | 9 | 10 | 20 | 40 |
| 1 | 7.04E–06 | 7.34E–06 | 8.03E–06 | 9.14E–06 | 9.12E–06 | 9.94E–06 |
| 2 | 5.46E–06 | 7.63E–06 | 9.01E–06 | 8.96E–06 | 1.06E–05 | 1.04E–05 |
| 3 | 6.47E–06 | 7.68E–06 | 8.76E–06 | 7.71E–06 | 1.02E–05 | 1.01E–05 |
| Mean | 6.32E–06 | 7.55E–06 | 8.60E–06 | 8.60E–06 | 9.97E–06 | 1.02E–05 |
| St. Dev. | 8.02E–07 | 1.81E–07 | 5.07E–07 | 7.81E–07 | 7.63E–07 | 2.25E–07 |
| CV % | 12.6885 | 2.39723 | 5.89705 | 9.08262 | 7.65 | 2.21985 |

The measurements of silver ions are time-independent, whereas measurements of silver nanoparticle are time-dependent. This demonstrates that the positive potential has an influence on the measurement signal (see FIG. 17).

As shown in FIG. 18, the second method was to keep the pre-treatment time the same (10 s) and vary the potential of the pre-treatment.

The current signal from $Ag^+$ is potential-independent; the signal from silver nanoparticle is potential dependent.

The potential has no effect at all on the silver ions but it strongly affects silver nanoparticle. These data show that the electroactive species measured during the last step of ASV of silver nanoparticle is created during the pre-treatment time. The silver nanoparticle and its charged coverage is migrated to the electrode via a potential gradient. The positive potential at the electrode dissolves the silver nanoparticle to silver ions. The silver ions can therefore be accumulated on the electrode and stripped off for measurement. The skilled person would know how to do this.

EXAMPLE 9

An electrochemical immunoassay was carried out as follows:
Silver Nanoparticles and Antibody Conjugation:
1. Spin down 10 ml of silver nanoparticle (British Biocell) in 5×2-ml-tubes (13 200 rpm, 5 mins, 4° C.).
2. Discard the supernatants and combine all 5 pellets in one tube so that the final volume of silver nanoparticle is 1 ml.
3. Add an antibody solution (Hytest) to obtain desired concentration (~0.05 mg/ml).
4. Incubate for 40 mins on a roller mixer.
5. Centrifuge at 13 200 rpm, 5 mins, 4° C. (salvage the nanoparticle from the supernatant if necessary).
6. Resuspend the pellet in 1 ml of blocking buffer (3% BSA).
7. Incubate for 40 mins on the roller mixer.
8. Spin down at 13 200 rpm, 5 mins, 4° C. (salvage the nanoparticle from the supernatant if necessary).
9. Wash the pellet by resuspending it in 1 ml of 0.1M borate buffer pH 7.5, then spin it down (13 200 rpm, 5 mins, 4° C.), (salvage the nanoparticle from the supernatant if necessary) and then again resuspend it in 1 ml of 0.1M borate buffer pH 7.5.
10. Store at 4° C. until used.
Electroimmunoassay:
1. Coat the plate with 50 µl of first antibody solution (10 µg/ml in PBS)
2. Incubate overnight at 4° C. (plate sealed).
3. Wash 3× with 200 µl of washing buffer.
4. Add 150 µl of blocking buffer (Pierce #37536) and incubate 30 mins on a shaker.
5. Wash 3× with 200 µl of washing buffer.
6. Prepare the first concentration (the highest) of the analyte in wash buffer and perform serial dilutions in wash buffer.
7. Add 50 µl of analyte solutions and incubate 30 mins on the shaker.
8. Wash 3× with 200 µl of wash buffer.
9. Dilute silver nanoparticle-antibody conjugate 5× in wash buffer and add 50 µl of it to the wells. Incubate 1 h on the shaker.
10. Wash 3× with 200 µl of wash buffer.
11. Store at 4° C. overnight (sealed and without wash buffer)
12. Add 50 µl of 1M $NH_4SCN$ and shake on the mixer for 1 h.
13. Apply the solution from each well on the surface of carbon paste electrode and run anodic stripping voltammetry (ASV).

The steps of ASV are the following:
a) Step: +0.4V for 10 s (pre-treatment)
b) Linear sweep: 0.0V→–1.6V at scan rate=1V/s and step potential=0.005V
c) Step: –1.6V for 5 s (nucleation)
d) Step: –1.2 V for 55 s (deposition [reduction] of electroactive species)
e) Linear sweep: –1.2V→+0.1V at scan rate=1V/s and step potential=0.01V (stripping [oxidation] of electroactive species). During this sweep a peak current is generated and the area under the peak (i.e. number of coulombs) is proportional to the concentration of electroactive species.

The potential is referenced to the reference electrode. The reference electrode is typically a D2 carbon ammonium thiocyanate reference electrode.

EXAMPLE 10

Assays for Myoglobin Looking at the Amount of Anti-myoglobin Hytest 4E2 Antibody Required for the Maximum Sensitivity of the Assay The concentration of coating antibody does not greatly affect the assay. The sensitivity was very good for varying amounts of 4E2 antibody and the calibration curves are very similar (5, 10 and 15 µg/ml) as shown in FIG. 19. However too high concentration of coating antibody can negatively influence the assay. This is very much dependent on the antibody used and the surface to which it is attached. The sensitivity obtained is good, with a plateau reached at about 50 ng myoglobin/ml. This sensitivity is similar or even better than the classical ELISA based on enzymatic detection of analyte.

A release agent such as a thiol with a charged unit is added to the solid phase analyte silver nanoparticle complex. Examples of suitable release agents include ammonium thiocyanate and potassium thiocyanate. Alternatively, a thiosulphate could be used. Thiols are preferred as they bind to silver more effectively than other agents.

The thiol weakens the antibody interaction so that the silver nanoparticle is released from the complex. The charged thiol also forms a layer around the silver nanoparticle making the particle charged, and allowing it to be electrically migrated to the electrode where the measurement takes place. Measurement can be conducted using ASV. ASV is an analytical technique that involves preconcentration of a metal phase onto an electrode surface and selective oxidation of each metal phase species during an anodic potential sweep. The silver-thiol charged nanoparticle is electroactive and stable. The electroactive charged nanoparticle can be electrochemically plated onto an electrode as a pre-concentrating step. Once at the electrode, the silver nanoparticle is electrochemically dissolved by oxidising under a positive potential. The ions are plated on the electrode by reversing the potential to a negative potential. The silver plate is then electrochemically stripped off the electrode (by once again applying a positive potential) giving a stronger silver peak signal. The amount of silver ions stripped off the electrode can be related to the number of silver nanoparticles used to give a signal which relates to the number of analytes captured on the solid phase of the assay.

Instead of a "sandwich" or non-competitive immunoassay as described above, other formats could equally be used to capture the silver particles such as a competition immunoassay or a hapten-based assay. Such assays are well known.

Metal nanoparticles are commercially available and may be conjugated to binding moieties by known methods.

The binding moiety may be anything capable of binding to the analyte to be detected e.g. protein, peptide, antibody or fragment thereof, nucleic acid.

The first binding moiety need not be immobilized on a solid support.

EXAMPLE 11

Charged silver nanoparticles were prepared as described above with respect to Example 4 (without ferricyanide) except that 1M thiosulphate was used as the release agent. The silver nanoparticle-thiosulphate species was measured by ASV.

Figure 20:
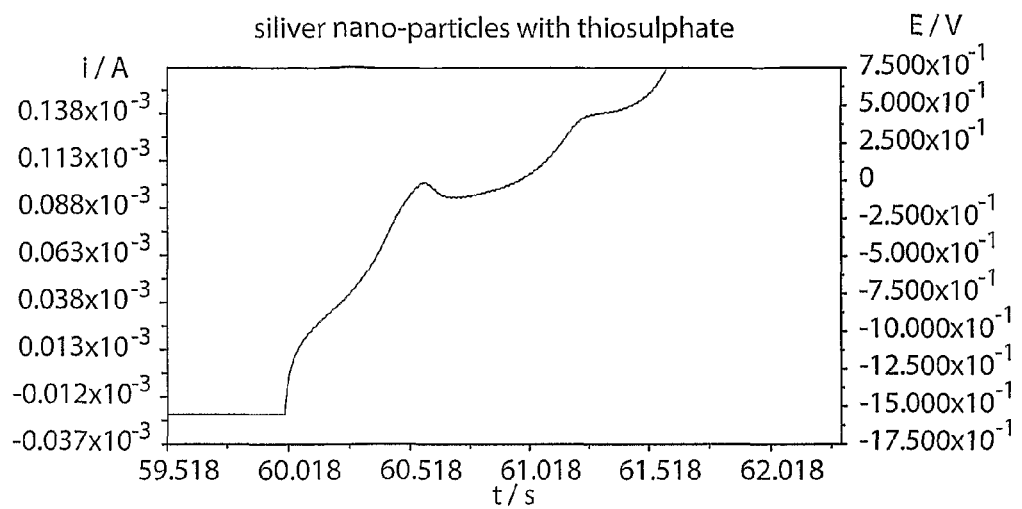

The results are shown in FIG. 20, and demonstrate that thiosulphate is a suitable release agent for use in this method.

EXAMPLE 12

Figure 21:
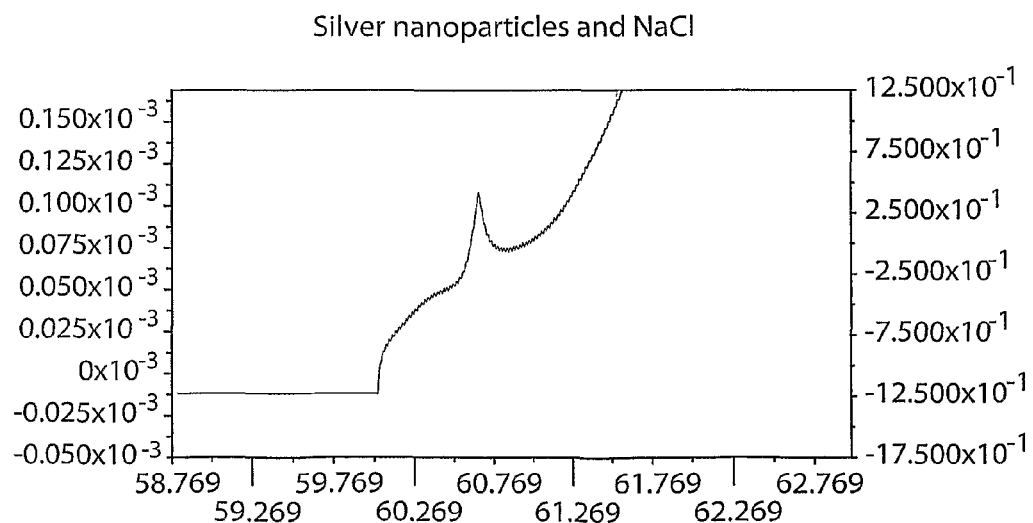

The experiment of Example 11 was repeated, but 1M NaCl was used as the release agent. The results illustrating that NaCl is a suitable release agent are shown in FIG. 21.

EXAMPLE 13

Figure 22:
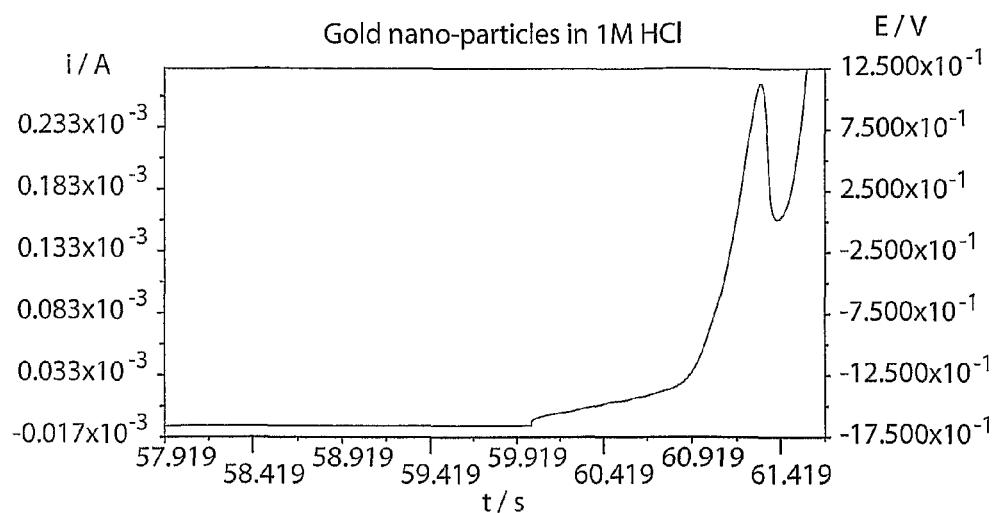

The experiment of Example 11 was repeated but gold nanoparticles were used instead of silver nanoparticles. 1M HCl was used as the release agent. The results are shown in FIG. 22.

EXAMPLE 14

Figure 23:
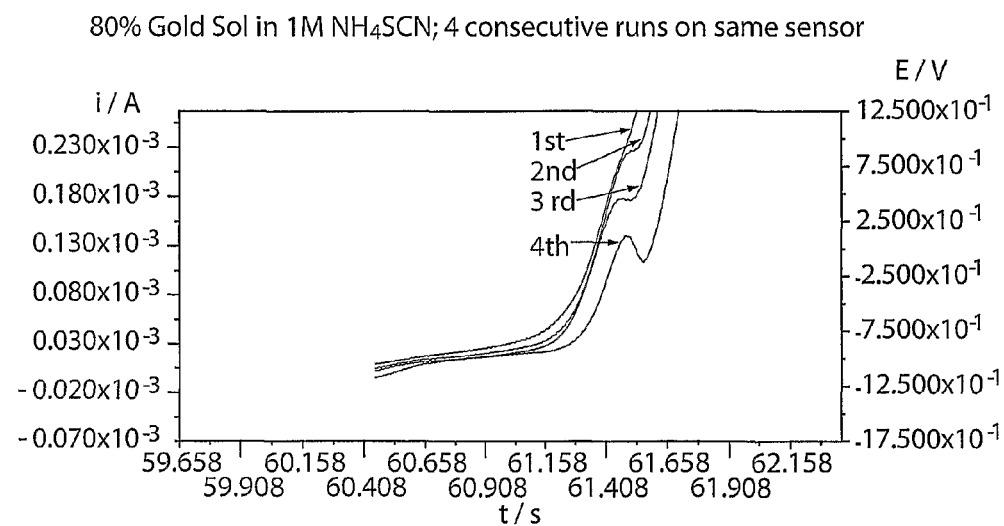

The experiment of Example 13 was repeated, but 1M thiocyanate was used as the release agent. The results are shown in FIG. 23.

COMPARATIVE EXAMPLE 15

ASV was carried out an gold and silver nanoparticles in the absence of a charged release agent. FIGS. 24 (gold) and 25 (silver) illustrates that no peak is observed when the nanoparticles are uncharged.

In a modification, two different analytes within a same sample can be detected by using both gold and silver nanoparticles. In this case, gold nanoparticles are attached to a first binding moiety that recognises a first analyte. Gold ions and silver it give different distinguishable peaks when measured on the same electrode by ASV.

A kit may be provided. The kit may comprise a metal label for binding to an analyte, at least one release agent for releasing the metal agent once bound to an analyte and for forming a charged nanoparticle with the metal label, a device having at least one zone for binding the metal label to an analyte and at least two electrodes. Optionally, the kit may contain a binding moiety capable of binding to the analyte of interest and labelled with a metal label. The device may be a multiwell plate.

The disclosures in GB 0723137.6 and GB 0812845.6, from which the present application claims priority, and in the Abstract accompanying this application are incorporated herein by reference.

The invention claimed is:

1. A method for determining the presence or amount of a metal-labelled analyte in a sample, the method comprising the steps of:
   Adding a release agent to the metal-labelled analyte to release the metal label from the analyte, the release agent and the metal label together forming an insoluble charged species,
   Applying a potential to bring the insoluble charged species to an electrode,
   Applying a positive potential to the insoluble charged species to dissolve the metal label to form metal ions, and
   Carrying out a quantitative determination procedure to determine the presence or amount of the metal-labelled analyte,
   Wherein the release agent comprises thiosulphate, a charged thiol chain, ammonium thiocyanate, potassium thiocyanate or NaCl.

2. A method as claimed in claim 1, wherein the charged species is brought to an electrode by applying a positive potential, the positive potential also resulting in the formation of the metal ions.

3. A method as claimed in claim 1, wherein the charged species is negatively charged.

4. A method as claimed in claim 1, wherein the release agent is a charged thiol chain.

5. A method as claimed in claim 1, wherein the release agent is ammonium thiocyanate or potassium thiocyanate.

6. A method as claimed in claim 1, wherein the release agent is a thiosulphate.

7. A method as claimed in claim 1, wherein the release agent is NaCl.

8. A method as claimed in claim 1, further comprising the step of labelling the analyte with the metal label wherein the analyte is incubated with a binding moiety capable of binding to the analyte and which is labelled with the metal label.

9. A method as claimed in claim 8, further comprising the step of incubating the analyte with a further binding moiety capable of binding to the analyte and which is secured to a solid support.

10. A method as claimed in claim 9, wherein the solid support is mobile or fixed.

11. A method as claimed in claim 10, wherein the mobile solid support is magnetized.

12. A method as claimed in claim 9, wherein the metal label is a metal nanoparticle and wherein the solid support is a particle that is larger or smaller than the metal nanoparticle so as to allow filtering of unbound from bound metal nanoparticles.

13. A method as claimed in claim 9, wherein the solid support is a charged particle in order to enable electrical separation.

14. A method as claimed in claim 9, wherein the fixed solid support is a three-dimensional surface or structure or a two-dimensional surface or structure.

15. A method as claimed in claim 14, wherein the fixed solid support is a three-dimensional porous structure.

16. A method as claimed in claim 1, wherein the metal label is a particulate label or a nanoparticle.

17. A method as claimed in claim 16, where the metal label is a silver nanoparticle or a gold nanoparticle.

18. A method as claimed in claim 1, wherein the quantitative determination procedure is a voltammetric method.

19. A method as claimed in claim 18, wherein the voltammetric method is anodic stripping voltammetry.

20. A method as claimed in claim 1, wherein the release agent forms a charged layer on the surface of the metal label to enable it to be moved under an electrical potential.

* * * * *